United States Patent [19]

Hollinger et al.

[11] 4,395,676
[45] Jul. 26, 1983

[54] FOCUSED APERTURE MODULE

[75] Inventors: John D. Hollinger; Michael R. Groves; Walter R. Hogg, all of Miami, Fla.

[73] Assignee: Coulter Electronics, Inc., Hialeah, Fla.

[21] Appl. No.: 209,611

[22] Filed: Nov. 24, 1980

[51] Int. Cl.³ ............................................. G01N 27/00
[52] U.S. Cl. ..................................... 324/71.4; 377/10
[58] Field of Search ............... 324/71 CP; 235/92 PC

[56] References Cited

U.S. PATENT DOCUMENTS

| | | | |
|---|---|---|---|
| 2,656,508 | 10/1953 | Coulter | 324/71 CP |
| 3,299,354 | 1/1967 | Hogg | 324/71CP |
| 3,549,994 | 12/1970 | Rothermel | 324/71 CP |
| 3,710,933 | 1/1973 | Fulwyler | 324/71 CP |
| 3,793,587 | 2/1974 | Thom | 324/71 CP |
| 4,001,678 | 1/1977 | Berg | 324/71 CP |
| 4,014,611 | 3/1977 | Simpson et al. | 324/71 CP |
| 4,165,484 | 8/1979 | Haynes | 324/71 CP |

Primary Examiner—Michael J. Tokar
Attorney, Agent, or Firm—Gerald R. Hibnick

[57] ABSTRACT

A particle analyzer for a sample suspension of particles originating in a container in which: a flow director is mounted between the container and a first chamber, a particle sensing aperture is mounted between the first chamber and a second chamber, a liquid sheath is introduced into the first chamber for hydrodynamically focusing the particles through the sensing aperture, an electrical current passes through the sensing aperture for generating impedance signals, the pressure drop is regulated across the flow director to assure a constant flow of the suspension through the flow director and the aperture, and the flow director is formed into an optical element for viewing the sensing aperture.

14 Claims, 5 Drawing Figures

Fig-5.

FOCUSED APERTURE MODULE

BACKGROUND OF THE INVENTION

1. Field of the Invention

This invention relates generally to the art of studying the physical properties of microscopic particles carried in suspension and, more particularly, is concerned with improved structure for obtaining signals from hydrodynamically focused particles passing through a sensing aperture mounted in a module.

2. Description of the Prior Art

The type of particle analyzer, in which the teachings of the present invention are intended to be utilized, first was disclosed in U.S. Pat. No. 2,656,508 and operates on a principle often referred to as the principle of Wallace H. Coulter and improved upon as taught in U.S. Pat. No. 3,299,354 to Hogg. According to this principle, the passage of a microscopic particle suspended in a conducting liquid through a sensing aperture, having dimensions which are approximately ten times larger than that of the particle, causes a change in the impedance of the electrical path through the liquid contained in the aperture. The magnitude of this change is, under ideal conditions, approximately proportional to the volume of the particle. The particle analyzer typically includes a pair of electrodes positioned on either side of the sensing aperture. An electrical power source is coupled to the electrodes and a signal detecting circuit is connected across the electrodes, so that the signal detecting circuit will sense only impedance changes caused by the passage of a particle through the sensing aperture. These signals commonly are referred to as particle pulses and are fed from an amplifier to other electrical circuitry for the analysis of the pulse height and for counting the pulses.

Examples of particle analyzing devices having the structure and associated electrical circuitry described above can be found in products sold under the trademark COULTER COUNTER, which is a registered trademark of Coulter Electronics, Inc., Hialeah, Fla.

The pulse signal produced when a particle passes through the aperture depends not only on the particle size or volume, but also to a lesser extent on its shape, orientation, and its path near and through the aperture. For example, the amplitude-time history of the pulse signal for a particle moving near the aperture wall is different from that of a particle moving through the center of the aperture. To provide for better resolution of signals from closely sized particles, which are influenced by the above-described factors, several apparatuses have used "hydrodynamic focusing" techniques.

The most relevant apparatus using hydrodynamic focusing is shown in FIGS. 5 and 6 of U.S. Pat. No. 4,014,611 to Simpson et al., owned by the same assignee as that of the present invention. In this arrangement a nozzle is positioned between a bath of suspended particles and an aperture disk containing the sensing aperture, so as to define a sheath chamber therebetween. A passageway provides clean electrolyte to the sheath chamber. A liquid sample suspension of particles proceeds from the nozzle. The electrolyte in the sheath chamber forms a generally tubular sheath flow around the sample suspension. The hydrodynamic pressures of the sheath reduces the diameter of the sample suspension stream and centers it in a direction coaxial with the center axis of the sensing aperture. In this manner, the particles are hydrodynamically focused to travel in essentially the same path through the sensing aperture, thereby giving better signal resolution.

The above-described arrangement of U.S. Pat. No. 4,014,611 has several disadvantages when used in sophisticated commercial structures. First, the amount of sample suspension being processed cannot be simply and economically regulated or measured. More specifically, a regulator maintains a substantially constant pressure drop, and therefore a substantially constant flow, across the sensing aperture. Consequently, when there are variations in the amount of sheath liquid passing through the sensing aperture, there are forced variations in the flow of the sample suspension, since the total flow through the sensing aperture is held constant. Another problem is that even without such flow variations, to obtain a desired rate of flow of the sample suspension through the aperture, it is necessary to fix the rate of flow of the sheath liquid with respect to the rate of flow of sample suspension. Therefore, to obtain a constant non-fluctuating sample flow at a desired rate (i.e., fixed sheath to sample ratio) through the sensing aperture with this device, it is necessary in the prior art arrangement accurately and precisely to control both the sample suspension flow through the nozzle and the sheath flow, in addition to regulating the pressure drop across the sensing aperture. Second, the nozzle blocks the optical viewing of the sensing aperture, thereby preventing monitoring of the sensing aperture for possible clogging by debris. Third, since the upstream electrode is positioned on the upstream side of the sensing aperture, even the relatively large constrained path of the nozzle can introduce some signal noise, which causes a poorer signal to noise ratio. Fourth, the protruding end portion of the nozzle is unduly fragile and awkward for use in a commercial apparatus.

As discussed with U.S. Pat. No. 4,014,611, the hydraulic systems of the prior art for regulating and measuring the sample suspension through the sensing aperture require the control of the sample suspension flow and the sheath flow. The regulation of these flows require elaborate arrangements, such as the dual pistons of U.S. Pat. No. 4,001,678 to Berg. The Berg patent discloses another hydrodynamic focusing system using a liquid sheath around a sample suspension, wherein the pair of pistons force a quantity of liquid from a chamber downstream of a sensing aperture and also force a lesser quantity of liquid into a sheath chamber upstream of the sensing aperture, with the difference in the two quantities of liquid being made up by a quantity of sample suspension, which proceeds from a sample container, through a nozzle and into the sheath chamber.

U.S. Pat. No. 3,793,587 to Thom et al., assigned to the assignee of the present invention, discloses two dividing walls, each having an orifice and two sheaths for hydrodynamic focusing in successive chambers. The construction of this arrangement prevents the accurate measurement and regulation of sample suspension, which is sensitive to variation in the sheath flow and optical viewing of the sensing apertures.

Another hydrodynamic focusing arrangement is disclosed in an article entitled "Improved Resolution in Coulter Counting by Hydrodynamic Focusing", JOURNAL OF COLLOID AND INTERFACE SCIENCE, Vol. 26, pp. 175–182(1968). In this apparatus an elongated protrusion, mounted on the sample vessel, causes the suspension to be accelerated and thinned by a sheath of electrolyte prior to passing through the sensing aperture. Again, this arrangement has the inability simply to meter the sample volume and view the aperture as described with respect to the above-described devices.

U.S. Pat. No. 3,710,933 to Fulwyler et al., discloses a hydrodynamic focusing apparatus wherein the sample suspension is provided by a sample introduction tube and the liquid sheath is provided by a sheath tube positioned in surrounding, coaxial relationship to the sample introduction tube. A microscopic sensing aperture is positioned at the end of the sheath tube. In addition to the above described deficiencies, the tubes are very susceptible to breakage, due to the extremely small size.

U.S. Pat. No. 3,739,628 to Karuhn et al. discloses a flow straightener means in the form of a flow directional collar. However, there is no sheath for surrounding the sample suspension and the collar merely reduces flow turbulence, while directing particles along a path somewhat coaxial with the center axis of the sensing aperture. Hence, there is no hydrodynamic focusing using a liquid sheath.

U.S. Pat. Nos. 2,656,508 to Coulter, 3,299,354 to Hogg, and 4,014,611 to Simpson et al. are incorporated herein as a part hereof by specific referece.

SUMMARY OF THE INVENTION

The invention relates to a particle analyzing apparatus for detecting the properties of particles and comprises a container of a liquid suspension of the particles to be analyzed, a first chamber and a second chamber. A holder forms a wall between the container and the first chamber. The director holder has a flow director provided therein to form a liquid passageway between the container and the first chamber. An aperture holder forms a wall between the first chamber and the second chamber and has a sensing aperture provided therein to form a constricted liquid passageway between the first chamber and the second chamber. An electrical current is provided through the sensing aperture to generate detectable electrical signals with the passage of the particles through the sensing aperture. A particle free liquid is provided to the first chamber for forming a liquid sheath around a quantity of the liquid suspension from the flow director. A constant, substantial pressure drop is provided across the flow director to move the quantity of the suspension liquid from the container to the first chamber, so that the constant pressure drop establishes a constant flow rate of the suspension liquid into the first chamber and hence through the sensing aperture. The flow director has an elongated bore for passing the suspension liquid. The bore is dimensioned to form a hydraulic resistor to limit the flow of the suspension liquid therethrough, thereby providing a quantitatively, highly accurate stream of individual particles. Additionally, a manometer, due to the substantial pressure drop, can be operative for measuring such pressure drop.

Other aspects of the invention include designing the flow director with a pair of opposed lens surface and forming the same out of a transparent material, so as to allow optical viewing of the sensing aperture to monitor the same for debris and like clogging materials. Additionally, an electrode with a low resistance is positioned in traversing relationship to the director holder, and thereby shunts the relatively high electrical resistance of the liquid passageway of the flow director. Also, the flow director is threaded so as to be removable, thereby allowing ready access and cleaning of the chambers.

As previously mentioned, the prior art particle analyzers have regulated and monitored the pressure drop across the sensing aperture to assure a relatively constant sample flow of liquid suspension. Contrary to this prior art practice, the pressure drop across the flow director of the present invention is regulated and monitored to achieve the constant sample flow. This regulation and monitoring is feasible, from a practical standpoint, only because there is generated a substantial pressure drop across the flow director. The substantial pressure drop is implemented by the bore of the flow director which is formed into a hydraulic resistor for limiting the sample flow, so as to provide an entrained stream of individual particles. In those prior art particle analyzers having a sample introduction nozzle, the directing bore forming therein do not provide any substantial flow resistance.

It was discovered by the applicants herein that, contrary to the teachings of the prior art, the sample suspension containing the particles need not be introduced into the sheath liquid by narrow, tube-like nozzles of the prior art to achieve the objective of having the sample suspension and the sheath flow in the same direction. To the contrary, it was found that the sheath liquid flow takes an abrupt turn under the planar or lens-like end of the flow director and immediately forms the desired cylindrical liquid sheath around the sample suspension. By virtue of this discovery, the continuously planar or lens-like design of the end of the flow director not only permits the incorporation of the previously described optical features, but also allows for a compact mechanical design for the nozzle, which provides substantial structural strength compared to the fragile and awkward tube-like nozzles of the prior art.

As previously mentioned, one of the disadvantages of the prior art focusing arrangements is that optical viewing and monitoring of the sensing aperture was not possible, due to the obstruction of the viewing path by the non-planar surfaces of the sample introduction nozzles. Consequently, the applicants provided the flow director with optical surfaces for transmitting the light in a relatively organized or focused beam through the sensing aperture.

BRIEF DESCRIPTION OF THE DRAWINGS

Further objects and advantages of the present invention will become apparent as the following description proceeds, taken in conjunction with the accompanying drawing in which.

DESCRIPTION OF THE PREFERRED EMBODIMENTS

Figures 1, 3, 4:
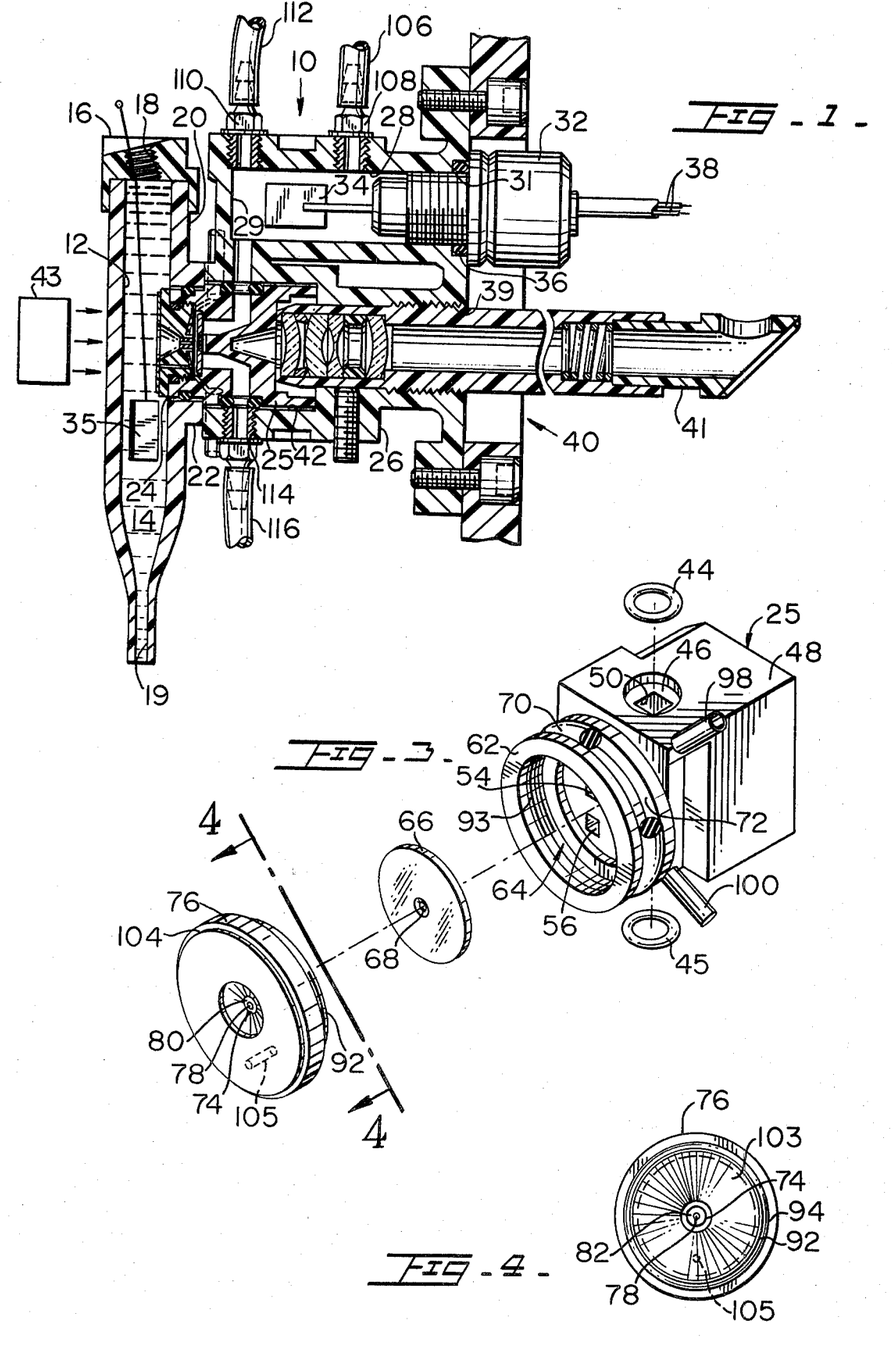
FIG. 1 is a cross-sectional side view of the particle analyzer embodying the invention.
FIG. 3 is an enlarged exploded perspective view of the aperture unit of FIG. 1.
FIG. 4 is a rear view of the nozzle holder taken on line 4—4 in FIG. 3.

Referring to FIG. 1, the aperture module of the invention is referred to generally by the reference numeral 10 and is an improvement upon the aperture module disclosed in U.S. Pat. No. 4,014,611. A container 12 retains a body of sample suspension 14 to be tested. There is a cover plate 16 with a sample supply port 18 for filling the container 12 and there is a drain opening 19 connected to suitable conduits and valve members (not shown) for selectively draining the container 12 when desired. One side wall 20 of the container 12 has an annular boss 22 formed integrally therewith, having a coaxial passageway 24 communicating with the interior of the container 12. In the embodiment shown, there is only one such boss 22 and a corresponding aperture unit 25 mounted on the container 12. Commercial COULTER COUNTER ® electronic particle analyzing devices preferably utilize three such units 25 in fluid communication with the container 12, although an operable particle analyzing device only requires one.

The aperture module 10 is comprised of a housing part 26 with a chamber 28 formed therein. The chamber 28 has a blind end 29 and is adapted for receipt in an open end 31 of an electrode cable assembly 32, which carries a signal electrode 34 for the device of which the module forms a part. A ground electrode 35 is provided in the container 12 as is required in such device. The assembly 32 is sealingly engaged in the chamber 28 by any suitable means, such as an O-ring 36, to prevent escape of fluid from the open end 31 of the chamber 28. Electric leads 38 couple the electrode 34 with a detector (not shown) of the device. A chamber 39 extends through the housing 26 and is adapted for receipt of an objective lens assembly 40 which is provided for visually examining the microscopic aperture path or opening in a hereinafter described aperture holder of the module. The lens assembly 40 illustrated in FIG. 1 includes a mirror assembly 41 for projection of an image of the aperture path on a screen; although the assembly 40 can use a microscope without the assembly 41. A generally rectangular socket 42 is provided as an extension of the chamber 39 and will be occupied, and hence closed off, when the aperture unit 25 is engaged therein as explained. A light source 43 is provided on one side of the container 12 and is coaxially aligned with the lens assembly 40.

Figure 2:
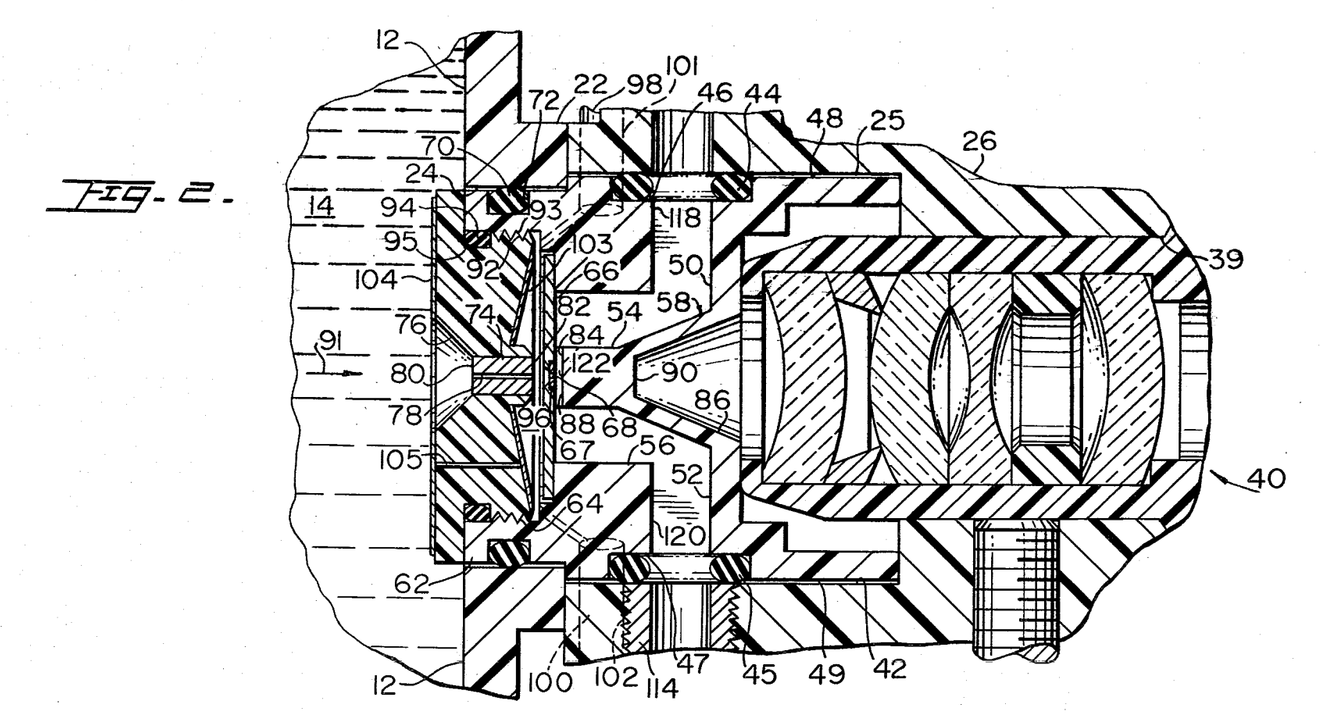
FIG. 2 is an enlarged, side elevational view of the aperture unit of FIG. 1.

Referring to FIGS. 2, 3, and 4, the aperture unit 25 is removably retained within the socket 42 of the housing 26 by a pair of O-rings 44 and 45, which are disposed in a pair of annular pockets 46 and 47 provided on opposite sides 48 and 49 of the aperture unit 25. The O-rings 44 and 45 engage the opposite inner facing surfaces of the socket 42 when the aperture unit 25 is secured in the socket 42 as described below.

The aperture unit 25 is formed of a block of transparent synthetic resin, such as high impact polystyrene or other material, which will not react with the reagents to which it will be exposed. The aperture unit 25 has a pair of vertically arranged passageways 50 and 52 and a pair of transverse passageways 54 and 56 interconnecting with the passageway 50 and 52, respectively. The vertically arranged passageways 50 and 52 open on the sides 48 and 49, respectively, of the aperture unit 25 in the annular pockets 46 and 47. The aperture unit 25 has an imperforate wall 58. The left hand part of the body of aperture unit 25 has a cylindrical extension 62 carrying a cavity or opening 64 which is adapted for receipt of an aperture holder or disc 66 for holding an aperture wafer 67 with an aperture 68 formed therein.

The aperture holder 66 is secured within the cavity 64 by cement or other suitable means. The extension 62, as previously mentioned, has an external configuration corresponding generally to the opening 24 in the boss 22 of the container 12 such that the module 10 is mountable upon the container 12 by telescopically engaging the extension 62 within the passageway 24. An O-ring 70 is disposed within a groove 72 upon the extension 62 to seal the extension 62 within the passageway 24 and prevent fluid leakage therefrom. The module 10, as heretofore described, is disclosed in the previously mentioned U.S. Pat. No. 4,014,611 and the specific structure thereof is per se not part of the invention.

The improvement of the device resides in the structure for providing hydrodynamic focusing of the particles while maintaining other design criteria. A flow director 74 is mounted in a director holder 76 in the form of carrier disc so that an elongated bore 78, formed in the flow director 74, is coaxially aligned with the aperture 68. In the preferred embodiment, the flow director 74 has a pair of opposed planar surfaces 80 and 82 and is formed of an optically transmissive material, such as glass. The wall 58 has a restriction portion 84 and the wall 58 defines on one side thereof a cavity 86, which is dimensioned and configured to receive a portion of the lens assembly 40. The restriction portion 84 has a pair of planar surfaces 88 and 90. Hence, light, in the direction of arrow 91, from the light source 43, passes through the planar surfaces 80 and 82 of the flow director 74, the aperture 68, the planar surfaces 88 and 90 of the restriction portion 84 and into the lens assembly 40. This arrangement provides the optical train for monitoring both the bore 78 and the aperture 68 to detect clogging of the same. Although planar surfaces are used for the flow director 74, the flow director 74 could have one or two slightly convex lens surfaces with a focal point at the aperture 68, for converging the light at the aperture 68. Hence, the flow director 74 can have any optical surfaces capable of providing an organized beam of light to illuminate the aperture 68, such surfaces being obvious to those skilled in the art. The director holder 76 and the passageway 24 are threaded so that the director holder 76 screws into the cylindrical extension 62, and thereafter can be removed by unscrewing. More specifically, the inner wall of the cylindrical extension 62 has a helix thread 92 formed therein and the periphery of the director holder 76 has a helix thread 93 formed therein to rotatably mate with the thread 92. An O-ring 94, disposed in a circular cutout 95 formed in the director holder 76, prevents electrolyte leaks.

A first or sheath chamber 96 is defined between the aperture holder 66 and the director holder 76. The aperture holder 66 is made as thin as practical to minimize the amount of space it occupies. A pair of sheath tubes 98 and 100 are mounted at the top and bottom of the sheath chamber 96, respectively, and are in fluid communication therewith so as to provide a sheath liquid, preferably in the form of a clean electrolyte. Cutouts 101 and 102 are formed in the corners of the socket 42 to allow the sheath tubes 98 and 100 to exit from the housing part 26 to an outside sheath liquid reservoir (not shown). Although only one sheath tube is necessary, at least two are preferable to allow the sheath chamber 96 to be flushed out. As the sample suspension is ejected from the flow director 76, a liquid sheath is formed around the sample suspension, which hydrodynamically focuses the particles as they pass through the sensing aperture 68. In this manner, all the particles which go through the flow director 76 go through the sensing aperture 68.

The surface of the director holder 76 facing into the sheath chamber 96 has mounted thereon a thin sheet-like electrode 103. On the opposed surface of the director holder 76 a second, thin sheet-like electrode 104 is mounted. The electrodes 103 and 104 are electrically interconnected by a wire 105, with all three components 103, 104 and 105 being formed preferably from platinum. When the director holder 76 is removed from the module, the electrodes 103 and 104 likewise are removed. Hence, the electrical circuit consists of an electrolyte path from the ground electrode 35 to the electrode 104, a metal path between the electrodes 103 and 104, and a second electrolyte path from the electrode 103 through the sensing aperture 68, to the signal electrode 34. As will become apparent hereinafter, the electrical resistance of the bore 78 is so high that the arrangement of the electrodes 103 and 104, which electrically shunts the bore 78 through the wire 105, essentially shorts out the electrical resistance of the bore 78. This arrangement circumvents the need for a high voltage supply for the aperture current and obviates the need to have a separately wired electrode in the sheath chamber 96, a difficult requirement in an assembly which fits into a 1.2 centimeters cube. The bore 78 serves as a hydraulic resistor to give a measurable and controllable flow of the sample suspension. Although the bore 78 also acts as an electrical resistor, it does not generate significant electrical noise, due to the shunting effect of electrodes 103, 104 and 105.

Referring again to FIGS. 1 and 3, a source of clean electrolyte (not shown) is supplied to the module 10 through a conduit 106, connected over a fitting 108 which opens into the chamber 28. Another fitting 110 opens into the chamber 28 and is connected by a conduit 112 to a scavenge isolator (not shown) for flushing and purging the module 10 of fluid which has been introduced thereto. A fitting 114 is threaded into the bottom wall of the socket part of the housing 26 with its passageway in alignment with and opening into the bottom pocket 47. When the fitting 114 is in position as shown in FIG. 1, it abuts against the O-ring 45 to compress the same and thereby firmly retain the aperture unit 25 in the socket 42. The fitting 114 opens into the socket 42 of the chamber 39 and is connected by a conduit 116 to a collecting container or isolator (not shown) to which a vacuum source can be applied. The passageway 50 in the aperture unit 25 opens at one end 118 thereof, to the chamber 28 and the passageway 52 opens at one end 120, to the fitting 114. The O-rings 44 and 45 seal the juncture of the passageways 50 and 52 at their open ends with the chamber 28 and the fitting 114 to provide liquid-tight connection therebetween. The restriction portion 84 extends within the fluid flow to a location in close proximity to the aperture 68, thereby forming a sweep flow region 122. Consequently, the sweep flow region 122, the passageways 50 and 52 and the chamber 28 all form a second chamber on the other or down stream side of the aperture 66, with respect to the sheath or first chamber 96. Clean electrolyte can be introduced to the sweep flow region 122 by drawing a vacuum through the conduit 106, which will cause the electrolyte to enter the chamber 28, pass therethrough into the passageway 50 through the end 118 thereof, around the restriction portion 84, and thereafter exit from the passageway 52 through the fitting 114 and the conduit 116 to the waste isolator. In a known manner, the clean electrolyte will sweep away the sample coming through the aperture 68 and prevent particles from straying in the sweep flow region 122, thus eliminating any swirling effect of undesirable eddy currents. The structure described in this paragraph is disclosed in the heretofore mentioned U.S. Pat. No. 4,014,611.

Figure 5:
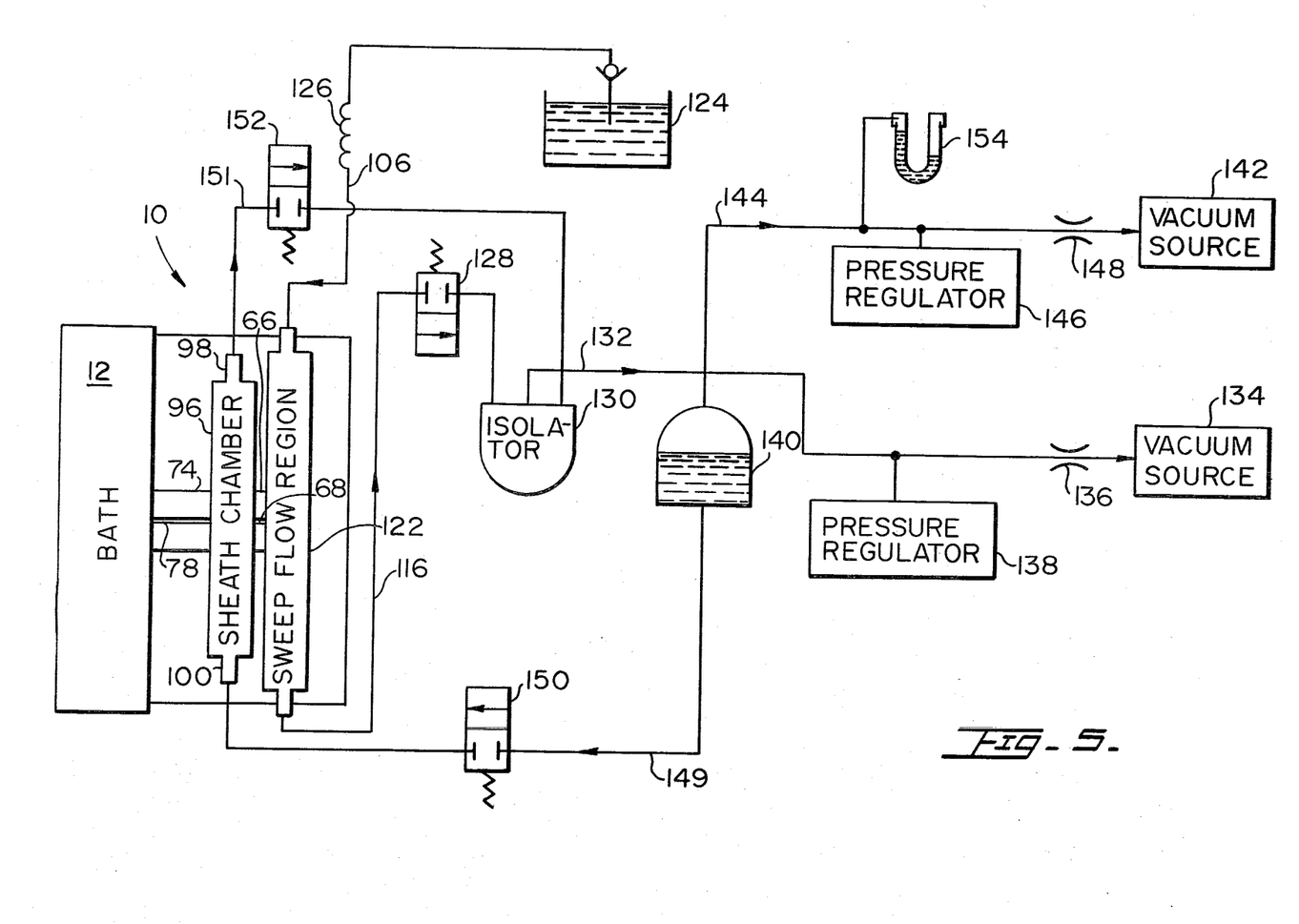
FIG. 5 is a schematic of the hydraulic system for the particle analyzer.

With reference to FIG. 5, the container 12, the flow director 74, the sheath chamber 96, the aperture holder 66, and the sweep flow region 122 are shown schematically to illustrate the hydraulic system for providing the fluid flows to the module 10. A saline solution is provided from a reservoir 124 to the sweep flow region 122 through the fluid line or conduit 106. The conduit 106 has a coil 126 formed therein to provide a large electrical resistor. The saline solution exits by way of the conduit 116, through a valve 128 to a vacuum isolating chamber 130, wherein droplets of the saline solution interrupt an electrical path that would have been formed through the liquid in the conduit 116. The vacuum isolating chamber 130 is connected by a fluid line or conduit 132 to a vacuum source 134 through a fluid resistor 136. A pressure regulator 138 is connected to the conduit 132 to regulate the pressure and, for example, to provide a negative pressure of forty-five centimeters of mercury. As FIG. 5 has been described to this point, the hydraulic system is of conventional design used with commercial products, as shown in U.S. Pat. No. 3,549,994 to Rothermel et al. In such prior art arrangements, contrary to the module 10 embodying the invention, a manometer normally would be connected to the conduit 132 to monitor the fluid pressure differential.

A reservoir chamber 140 is connected to a vacuum source 142 by a fluid line 144. A pressure regulator 146 and a fluid resistor 148 are operative to provide, for example, a negative pressure of fifteen centimeters of mercury. The chamber 140 is connected by a fluid line 149 through a valve 150 to the sheath chamber 96 so as to deliver a saline solution from the reservoir chamber 140. Additionally, the sheath chamber 96 is connected by a fluid line 151 through a valve 152 to the isolating chamber 130. When the valve 152 is opened, the sheath chamber 96 can be flushed.

The pressures and relative pressure differences can, for the hydraulic system, vary substantially. For example, the bath container 12 can be held at atmospheric pressure. Relative to the pressure of the container 12, which is at atmospheric pressure, the reservoir chamber 140, and therefore the sheath chamber 96, can be held at, for example, minus fifteen centimeters of mercury and the isolating chamber 130, and therefore the sweep flow region 122, can be held at, for example, minus forty-five centimeters of mercury. Hence, there is a fifteen centimeters mercury drop across the flow director 74 and a thirty centimeter mercury drop across the aperture holder 66. The mercury drop across the flow director can be reduced as low as two centimeters, if desired.

Contrary to prior art practices, pressure regulation for assuring a constant flow of the sample suspension containing particles through the aperture occurs by regulating, with the regulator 146, the pressure drop across the flow director 74 so as to maintain a constant pressure drop thereacross. By having the constant pressure drop across the flow director, the rate of flow of the sample suspension through both the flow director and the aperture remains constant, regardless of the sheath flow rate or the ratio of sample suspension to sheath liquid proceeding through the aperture 68. With a given, constant pressure drop and therefore a given, constant sample suspension flow through the flow director 74, the flow rate through the aperture 68, and therefore the sample suspension to sheath liquid ratio, is determined by the regulator 138. Moreover, the total flow through the aperture 68 can vary substantially without significantly affecting the included sample suspension flow; hence, the sample suspension is made essentially insensitive to the sheath flow. Also, contrary to the prior art practice, a manometer 154 is connected to the conduit 144 for monitoring the pressure drop across the flow director 74. More specifically, since the open end of the manometer 154 and the container 12 are at the same pressure, the manometer 154 measures the pressure drop across the flow director 74. Due to the formation of the flow director 74 into a substantially large hydraulic resistor, contrary to the sheath formation arrangements of the prior art, there is a sufficient pressure drop across the flow director 74 that it can be accurately measured and monitored by the manometer 154 and accurately regulated by the regulator 146 to maintain a constant pressure drop.

In the preferred embodiment, the bore 78 of the flow director 74 has, for example, a diameter of 50 microns and is 2.3 millimeters in length. With these dimensions, a fifteen centimeters mercury pressure drop across the flow director 74, and a diluted blood sample in the container 12, the sample particles will be sufficiently spaced apart and individually isolated while passing through the aperture 68. Although the pressure drop is held preferably at fifteen centimeters of mercury, the pressure drop can be reduced to as low as two centimeters of mercury and still be regulated and monitored in the manner previously described; however, such measurements are somewhat less accurate. Obviously, a given value of hydraulic resistance can be achieved by selecting the proper length and diameter of the bore 78. With a reduced pressure drop, the length of the bore 78 can be decreased and/or the diameter of the bore 78 can be increased with respect to the above illustrative values, and give the desired flow rate of the sample suspension. Hence, after selecting a given pressure drop above a minimum of two centimeters of mercury, the length and the diameter of the bore 78 are selected to give the desired flow rate of the sample suspension, which in turn determines the rate at which the particles are processed. The preferred dimensions given herein were chosen by calculating the requisite length of a commercially available capillary of the stated internal diameter, assuming the same pressure drop as was available in the unimproved apparatus.

Although a particular embodiment of the invention has been shown and described here, there is no intention to thereby limit the invention to the details of such an embodiment. On the contrary, the intention is to cover all modifications, alternatives, embodiments, usages and equivalents of the subject invention as fall within the spirit and scope of the invention, specification and the appended claims.

What is claimed is:

1. A particle analyzing apparatus for detecting properties of particles, said particle analyzing apparatus including a container for holding a liquid suspension of the particles to be analyzed, a first liquid holding chamber, a flow director having a bore which forms a liquid passageway between said container and said first chamber, a second liquid holding chamber, aperture means including a sensing aperture which forms a constricted liquid and electrical passageway between said first chamber and said second chamber, means for providing an electrical current through said sensing aperture to generate detectable electrical signals with the passage of the particles through said sensing aperture, fluid moving means for providing a pressure drop across said sensing aperture to move a quantity of liquid from said first chamber to said second chamber, means for providing a particle free liquid to said first chamber to form a liquid sheath around a quantity of said liquid suspension from said flow director, the improvement comprising:

means for providing a substantially constant pressure drop across said flow director to move said quantity of said liquid suspension from said container to said first chamber, whereby said substantially constant pressure drop establishes a substantially constant flow rate of said liquid suspension through said sensing aperture;

said bore of said flow director having an elongated configuration dimensioned to form a fluid resistor for limiting the flow of said quantity of said suspension through said bore, whereby said fluid resistor sufficiently restrains the flow therethrough to a desired flow rate so as to allow for said pressure drop across said flow director to be of a magnitude that is subject to regulation and measurement.

2. The particle analyzing apparatus according to claim 1, wherein said means for providing a pressure drop across said flow director is operative to provide a pressure drop of at least 1 inch of mercury.

3. The particle analyzing apparatus according to claim 1, wherein said means for providing a particle free liquid to said first chamber includes a liquid reservoir in fluid communication with said first chamber; said means for providing a pressure drop across said flow director includes means for maintaining said liquid reservoir at a predetermined pressure; and said apparatus further includes means for maintaining said container at a predetermined pressure which is higher than said pressure of said liquid reservoir.

4. The particle analyzing apparatus according to claim 3, wherein said means for maintaining said container at said predetermined pressure comprises said container being exposed to the atmosphere.

5. The particle analyzing apparatus according to claim 1, further comprising, a manometer operative to measure the pressure drop acorss said flow director.

6. The particle analyzing apparatus according to claim 5, further comprising, said manometer having one end in communication with said first chamber and the other end opened to the atmosphere.

7. The particle analyzing apparatus according to claim 1 or 5, wherein a director holder defines a wall between said container and said first chamber and has said flow director mounted therein; said means for providing an electrical current through said sensing aperture includes a first electrode disposed in said container, a second electrode disposed in said second chamber, and a third electrode mounted in said director holder; and said third electrode has a portion in fluid communication with said container and a portion in fluid communication with said first chamber, whereby said third electrode electrically shunts said liquid passageway formed by said flow director.

8. The particle analyzing apparatus according to claim 7, wherein said third electrode has an electrical resistance substantially less than the electrical resistance of said liquid passageway formed by said director bore.

9. The particle analyzing apparatus according to claim 7, wherein said portion of said third electrode in fluid communication with said container comprises a relatively thin first electrode portion mounted over a majority portion of the wall of said director holder facing said container, said portion of said third electrode in fluid communication with said first chamber comprises a relatively thin second electrode portion mounted over a majority portion of the wall of said director holder facing said first chamber, and said third electrode includes an interconnecting electrode portion which passes through said director holder and electrically couples said first electrode portion with said second electrode portion.

10. The particle analyzing apparatus according to claim 1 or 5 wherein said director holder is removably mounted between said container and said first chamber.

11. The particle analyzing apparatus according to claim 10, wherein said director holder has a disk-like configuration with a circular periphery, said periphery has threads formed thereon, and a juncture region between said container and said first chamber has threads formed therein for mating in rotatable engagement with said threads of said director holder.

12. The particle analyzing apparatus according to claim 1 or 5, wherein said flow director is formed of an optically transparent material, said flow director has a pair of optical lens surfaces, said optical lens surfaces of said flow director and said sensing aperture are coaxially aligned on an optical axis, and further including, a source of light aligned to provide an illuminating beam along said optical axis in the direction of said flow director and said sensing aperture, and an optical detection assembly positioned on the other side of said flow director and said sensing aperture relative to the side having said source of light, whereby monitoring of said sensing aperture can be accomplished.

13. The particle analyzing apparatus according to claim 12, wherein each said optical lens surface has a planar configuration.

14. For use in a particle analyzing apparatus of the Coulter type in which a particle sensing aperture provides the only fluid and electrical current paths between a body of liquid in a first chamber and a body of liquid in a second chamber, a sample suspension being caused to flow through said sensing aperture and into said second chamber; said apparatus also including a bore opening from a container into said first chamber for receiving the flow of sample suspension, particle free liquid being supplied into said first chamber for sheathing said flowing sample suspension as it passes from said bore; the improvement comprising, means for providing a relatively constant pressure drop across said bore to move said sample suspension from said container to said first chamber, whereby said substantially constant pressure drop establishes a substantially constant flow rate of said sample suspension through said sensing aperture; said bore being dimensioned to form a fluid resistor for limiting the flow of said sample suspension through said bore.

* * * * *

UNITED STATES PATENT AND TRADEMARK OFFICE
CERTIFICATE OF CORRECTION

PATENT NO. : 4,395,676

DATED : July 26, 1983

INVENTOR(S) : John D. Hollinger et al.

It is certified that error appears in the above—identified patent and that said Letters Patent is hereby corrected as shown below:

Column 3, line 24, change "referece" to --reference--;
          line 59, change "surface" to --surfaces--.
Column 10, line 46, change "acorss" to --across--.
Column 11, line 17, change "1 or 5" to --7,--.

Signed and Sealed this

Fifteenth Day of November 1983

[SEAL]

Attest:

GERALD J. MOSSINGHOFF

Attesting Officer

Commissioner of Patents and Trademarks